(12) United States Patent
Korzinov et al.

(10) Patent No.: US 6,871,089 B2
(45) Date of Patent: Mar. 22, 2005

(54) PORTABLE ECG MONITOR AND METHOD FOR ATRIAL FIBRILLATION DETECTION

(75) Inventors: Lev N. Korzinov, San Diego, CA (US); Dang V. Le, Carlsbad, CA (US)

(73) Assignee: Card Guard Technologies, Inc., San Diego, CA (US)

(*) Notice: Subject to any disclaimer, the term of this patent is extended or adjusted under 35 U.S.C. 154(b) by 412 days.

(21) Appl. No.: 10/163,972

(22) Filed: Jun. 5, 2002

(65) Prior Publication Data

US 2004/0010201 A1 Jan. 15, 2004

(51) Int. Cl.[7] .................... A61B 5/0404; A61B 5/0456; A61B 5/046
(52) U.S. Cl. ...................................... 600/518; 600/521
(58) Field of Search ................................ 600/508–509, 600/515–516, 518–519, 521; 607/25

(56) References Cited

U.S. PATENT DOCUMENTS 5,462,060 A * 10/1995 Jacobson et al. ........... 600/515
6,490,479 B2 * 12/2002 Bock .......................... 600/518
2003/0204215 A1 * 10/2003 Gunderson et al. ......... 607/27

* cited by examiner

Primary Examiner—Carl Layno
(74) Attorney, Agent, or Firm—Fulwider Patton Lee & Utecht, LLP

(57) ABSTRACT

An apparatus and method for detecting an atrial fibrillation through monitoring the R—R intervals of a patient's QRS complexes. Ratios of the current R—R interval are made to previous R—R intervals. Multiple moving averages are taken of the ratio results. The ratios are compared to a validating threshold and if the particular ratio is within a selected range, a moving average is calculated with inclusion of the present R—R interval. If the ratio is outside the range, a moving average is calculated without inclusion of the current R—R interval. The moving averages are combined and this difference average is compared to a trigger threshold. If the difference average exceeds the threshold, an atrial fibrillation is determined to exist, a memory trigger is provided, and the QRS complex data within a selected period of time about the atrial fibrillation event are recorded and removed from overwrite status in the memory. A reset threshold, differing from the trigger threshold, is used and if the difference average falls below the reset threshold, the method and apparatus are re-enabled to record a new AFIB event.

45 Claims, 5 Drawing Sheets

PORTABLE ECG MONITOR AND METHOD FOR ATRIAL FIBRILLATION DETECTION

BACKGROUND OF THE INVENTION

The present invention is directed to cardiac monitoring and recording apparatus and methods and, more particularly, to an apparatus and method for monitoring the heart activity of a cardiac patient, detecting atrial fibrillation, and recording related cardiac rhythm signals in real time for later interpretation and additional diagnostics.

Cardiac monitoring apparatus for monitoring and/or diagnosing cardiac arrhythmia in a hospital or clinical environment, such as in a cardiac care unit, are generally sophisticated systems. Power and data storage generally do not present significant concerns and excess data can be captured for diagnosis. Such sophisticated systems have not been found to be readily adaptable to ambulatory patients where battery power is required, and only limited digital storage or memory is available. Yet it is desirable to provide a portable system for ambulatory patients that can detect and record an atrial fibrillation event for later interpretation and additional diagnostics by a cardiac professional.

As is well known to those skilled in the art, atrial fibrillation is a potentially life threatening irregular cardiac rhythm. Atrial fibrillation is the irregular and rapid randomized contractions of the atria independently of the ventricles. The atria fire at a very rapid rate, up to 600 beats per minute. Instead of the heart contraction beginning at the sinoatrial node and being conducted to the ventricles, there is a rapid succession of beats at the atria. This localized contraction of the atrial muscle causes the waves to pass round and round in the atrium and leads to no atrial diastole and no atrial heartbeat. Fortunately, only some of these impulses make it through the AV node to depolarize the ventricles, resulting in an irregular ventricular rate. About five million patients are diagnosed with the condition per year, often too late for effective treatment.

The desirability of providing an electronic apparatus and method for automatically detecting atrial fibrillation ("AFIB") has been recognized for some time. Similarly, it has been recognized as desirable to provide both the detection and the recording of relevant electrocardiogram ("ECG") signals in a single portable unit that a cardiac outpatient can comfortably wear while the patient follows his daily routine. It is also desirable that such a unit has a low manufacturing cost so that it is more affordable and more patients can benefit from such a unit, yet be accurate so that false detections are avoided. Such a portable unit should be compact, rugged, and lightweight, battery operated with low power consumption, and yet responsive to atrial fibrillation. Similarly, the apparatus and the ECG processing methods it employs should be responsive to atrial fibrillation without being sensitive to extraneous false positives caused by noise or noncardiac muscular activity.

The introduction of large data memory sizes has made available an increased ability to more likely capture data relevant to any cardiac event. However, even large memory units are limited, and some restrictions on data capture must always be invoked. Some prior portable apparatus are programmed to operate continuously for twenty-four hours at which time the data must be uploaded to a central station either for analysis or for storage. Such a daily activity is undesirable where the patient may experience no atrial fibrillation or only a single AFIB event for longer periods of time. Instead, an adaptable system is preferable in which the unit can continuously monitor cardiac activity until an actual AFIB event is detected and captured in memory, the non-AFIB-related data being overwritten continuously. Data can be uploaded or transmitted when AFIB events have been captured.

Although AFIB events have been known to last for extended periods, it has become desirable to record limited data leading up to and following an AFIB event regardless of how long the event continues. For example, a time period of 45 seconds surrounding an AFIB event has been found to provide sufficient data for cardiac analysis. Prior devices, however, may record multiple portions of a particularly lengthy AFIB event indicating that the data represents multiple AFIB events, rather than only parts of a single lengthy one. Such excessive recording is inefficient for a portable unit. Battery power and memory are needlessly expended. Additionally, a cardiac professional's valuable time may be wasted attempting to study various recorded AFIB "events" when in fact the recordings are simply parts of a single event and may provide no further useful information. It has become desirable to provide a method and an apparatus that is better able to discern whether an AFIB event is a continuation of a previous one or is in fact a new event.

Other prior art apparatus contemplate only manually-activated recording when a wearer thinks that he is experiencing unusual heart activity, such as AFIB. The event recorder may be a credit card shaped device that the patient manually places over his heart when he feels that a cardiac "event" is occurring. The event recorder may also be mounted to the belt of the patient or be suspended about the neck of the patient with a lanyard and may take the form of a small pager-shaped device that is continually connected to the patient's chest skin via electrodes and a lead set.

Typically such event recorders "record" a patient's ECG for several minutes when a cardiac "event" is occurring in the patient. When the patient feels that an event is occurring, he activates the recording mode by pushing a button and the device begins recording. The recorder then records the ECG waveforms in digital form for later transmission over a telephone line or other digital communications means, such as through an RS-232 connection. Whenever patient transmission is required, the patient holds the speaker of the recorder to a telephone device mouthpiece (or connects another type of digital communications device) and uploads the recorded data to the computer of the health care facility providing cardiac monitoring services to the patient. The device includes a small speaker that converts the stored digital ECG data into audio form for transmission over the telephone line to a telephone receiver at his physician's office or other central medical facility. The audio data transmission is then converted back into digital and/or graphical form at the physician's office and the data examined.

In the past, such event recorders have been provided but simply record all ECG data occurring after a patient has activated the recorder. As discussed above, memories have limited capacities and in the case where a patient is under care only for the specific ailment of atrial fibrillation, only data leading up to, and following, an atrial fibrillation event may be of interest. Additionally, it has been demonstrated that persons are likely to only recognize about 20% of clinically significant events during waking hours, and even fewer while asleep. Thus, an automated AFIB detection system that accurately detects an AFIB event and automatically stores relevant data to that event is desirable.

Once a patient has been identified for AFIB monitoring, it is desirable to filter out other irregular cardiac rhythms, even though they may indicate the presence of heart disease. In particular, premature ventricular contraction or "PVC" (extra systole) is a cardiac contraction occurring before the normal one. PVC's should be ignored as they are not an AFIB event and it is not desirable to record ECG data surrounding such contractions. As another example, regularly recurring cardiac rhythms should be ignored as they also are not AFIB events. Bigeminy is a cardiac arrhythmia in which every other beat is a ventricular ectopic or premature ventricular contraction. Two beats follow each other in rapid succession, each group of two being separated by a longer interval. The initial beat is regarded as the normal one and is usually of greater intensity than the second one. Trigeminy is a series of three beats in rapid succession. Both bigeminy and trigeminy are irregular cardiac rhythms but they are not considered to be AFIB. It would be desirable to ignore them in monitoring a patient's cardiac rhythms for the existence of AFIB. Further, bigeminy and trigeminy have been found to regularly recur in a patient where AFIB is irregular.

It has been known to measure the R—R interval between sequential QRS complexes to detect cardiac arrhythmia. Running averages of the R—R interval have been used as well as other data processing techniques to identify various arrhythmia. However, these techniques have typically been used to identify a large set of arrhythmia and have not been focused on detecting and recording AFIB events. Such prior processing techniques do not clearly identify to a cardiac professional that an AFIB event has occurred and typically, extensive irrelevant ECG data must be examined to locate the actual AFIB event therein, if one even occurred. PVC's as well as regularly recurring arrhythmia (bigeminy and trigeminy) may trigger the recorder in the prior devices thereby using up valuable memory, battery power, and requiring unnecessary uploads of data when an AFIB event has not occurred. Thus, it would be desirable to more accurately recognize an AFIB event and record only ECG data related to that event.

Hence, a need has been recognized by those skilled in the art for an apparatus and a method for more accurate detection of AFIB, for fewer detections of false AFIB events and other non-AFIB events, and for uploading data from the portable unit to the central unit only when the portable unit has recorded AFIB data. Additional needs have been recognized for a light weight, portable unit that can be worn by a cardiac outpatient without substantially interfering with his daily routine, that is automatically responsive to AFIB events, that records only clinically significant AFIB events while minimizing false spurious recording, that significantly improves the power efficiency of the unit so as to permit batteries to last longer, and that has an enhanced signal-to-noise ratio for reduced sensitivity to extraneous or false positives. The present invention fulfills these needs and others.

SUMMARY OF THE INVENTION

Briefly and in general terms, the present invention is directed to an apparatus and method for monitoring the cardiac rhythms of a patient to detect AFIB while ignoring other arrhythmia, such as PVC's, bigeminy, and trigeminy. The QRS complex is referred to and, as well known to those skilled in the art, comprises certain waves seen in the electrocardiogram of a patient's cardiac rhythms. Multiple QRS complexes can be seen by reference to FIGS. 2A and 2B. The particular anatomical functions represented by the various parts of the QRS complex are well known to those skilled in the art and are not further discussed herein.

In particular, there is provided a method of analyzing the cardiac rhythms of a patient to detect the presence of atrial fibrillation comprising measuring R—R intervals of a plurality of QRS complexes of the patient, including the R—R interval between the present QRS complex and preceding QRS complex, comparing the present R—R interval to the preceding R—R interval to result in a first ratio, comparing the present R—R interval to the second preceding R—R interval to result in a second ratio, comparing the first ratio and the second ratio to a validating threshold for the selected number of QRS complexes, calculating a first average of R—R intervals without including the present R—R interval in the first average if the first ratio exceeds the validating threshold, calculating the first average of R—R intervals with inclusion of the present R—R interval in the first average if the first ratio is less than or equal to the validating threshold, calculating a second average of R—R intervals without inclusion of the present R—R interval in the second average if the second ratio exceeds the validating threshold, calculating the second average of R—R intervals with inclusion of the present R—R interval in the second average if the second ratio is less than or equal to the validating threshold, and determining the presence of an atrial fibrillation by analyzing the first and second averages.

In further aspects, the steps of calculating first and second averages comprise calculating exponential moving averages. The step of comparing the first ratio and the second ratio to a validating threshold comprises selecting the validating threshold so that R—R intervals caused by premature ventricular contractions and other irregular rhythms other than AFIB are excluded from the first and second averages.

In another aspect in accordance with the invention, the first and second averages are combined to result in a difference average and the step of determining the presence of an atrial fibrillation comprises comparing the difference average to a trigger threshold and if the difference average exceeds the trigger threshold, providing an indication that atrial fibrillation exists. The step of combining the first and second averages further comprises substantially nullifying regularly recurring irregular cardiac rhythms in determining the difference average, and in particular, nullifying bigeminy and trigeminy cardiac rhythms in determining the difference average.

In yet further aspects, the step of preventing the detection of an additional atrial fibrillation until the difference average is less than a reset threshold includes the reset threshold being different from the trigger threshold. Additionally, the reset threshold is selected to be a value that is far enough below the trigger threshold such that the step of providing an indication that atrial fibrillation exists is given substantially only for different occurrences of AFIB events in the patient.

In more detailed aspects, the steps of calculating the averages without inclusion of the present R—R interval comprises reducing the average from the previous average by a selected amount. The steps of comparing the current R—R interval to preceding R—R intervals comprises selecting the numerators and denominators of the ratios so that the results of the ratios are always greater than one. The steps of calculating averages each further comprises the step of selecting the number of R—R intervals in the averages so that the number of false atrial fibrillation detections is reduced and the number of missed detections of atrial fibrillations of the patient is reduced by means of adjusting the length of averaging. In one case, the number of R—R intervals used in calculating averages is selected to be approximately sixty.

In another more detailed aspect, a step of recording cardiac rhythms of the patient for a selected period of time in response to the provision of the indication that atrial fibrillation exists is performed. The recording of cardiac rhythms is conducted for a selected number of seconds before the atrial fibrillation is detected and a selected number of seconds after the atrial fibrillation is detected.

In additional aspects, a portable apparatus for analyzing cardiac rhythms of a patient to detect atrial fibrillation comprises a plurality of electrodes adapted for placement on the patient for developing electrical signals indicative of cardiac rhythms, a portable unit comprising a housing within which is located a battery for providing power to the portable unit, means for detecting R—R intervals of the QRS complexes of the patient, including and up to the present QRS complex, means for processing the detected R—R intervals to exclude R—R intervals generated by premature ventricular contractions, couplets, and by missed QRS detections, means for averaging R—R intervals, means for processing the averaged R—R intervals to substantially nullify regularly recurring irregular cardiac rhythms, and means for comparing the processed averaged R—R intervals to a threshold and for indicating the existence of an atrial fibrillation if the threshold is exceeded.

In more detailed apparatus aspects, the means for processing the detected R—R intervals comprise means for taking a ratio of the present R—R interval to the preceding R—R interval to result in a first ratio, means for taking a ratio of the present R—R interval to the second preceding R—R interval to result in a second ratio, and means for comparing the first ratio and the second ratio to a validating threshold. The means for averaging R—R intervals comprises means for calculating a first average of R—R intervals without including the present R—R interval in the first average if the first ratio exceeds the validating threshold, means for calculating the first average of R—R intervals with inclusion of the present R—R interval in the first average if the first ratio is less than or equal to the validating threshold, means for calculating a second average of R—R intervals without inclusion of the present R—R interval in the second average if the second ratio exceeds the first threshold, means for calculating the second average of R—R intervals with inclusion of the present R—R interval in the second average if the second ratio is less than or equal to the first threshold, and means for determining the presence of an atrial fibrillation by analyzing the first and second averages.

In other aspects, the means for processing the averaged R—R intervals to substantially nullify regularly recurring irregular cardiac rhythms comprises means for combining the first average and the second average such that regularly recurring irregular cardiac rhythms are subtracted from the first average to result in a lowered difference average. In particular, the means for combining subtracts bigeminy and trigeminy cardiac arrhythmia from the first average to result in a lowered difference average. The means for determining the presence of an atrial fibrillation is for comparing the difference average to a trigger threshold and if the difference average exceeds the trigger threshold, providing an indication that atrial fibrillation exists, and also for preventing the detection of an additional atrial fibrillation until the difference average, and in another aspect, the first average also, are less than a reset threshold, the reset threshold being different from the trigger threshold. In particular, the reset threshold is a value that is far enough below the trigger threshold such that the step of providing an indication that atrial fibrillation exists is given substantially only for different occurrences of atrial fibrillation events in the patient.

Other features and advantages of the present invention will become more apparent from the following detailed description of the invention when taken in conjunction with the accompanying drawings.

DETAILED DESCRIPTION OF THE PREFERRED EMBODIMENTS

Figure 1:
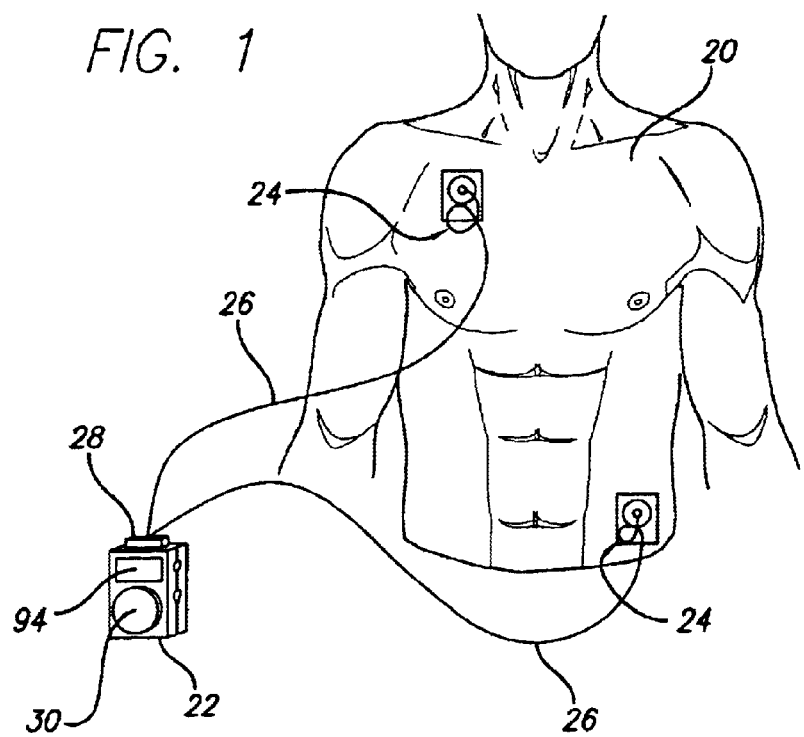
FIG. 1 is a simplified diagram of the use of a portable event recorder for detecting atrial fibrillation events in an ambulatory patient, and recording ECG signals relevant to such events.

Referring now to the drawings with more particularity, wherein like reference numerals in the separate views indicate like or corresponding elements, there is shown in FIG. 1 a patient 20 having a portable ECG event monitor and recorder unit 22. The portable event recorder 22 is battery powered and may be manufactured in accordance with many such units that exist today. The event recorder may be mounted to the belt of the patient 20 as shown or be suspended about the neck of the patient with a lanyard and may take the form of a small pager-shaped device that is continually connected to the patient's chest skin via electrodes 24 and a lead set 26, as shown. In this case a set of two electrodes 24 are attached to the patient's chest area by means known well to those skilled in the art. Other electrode configurations are equally applicable. The electrodes are used to receive signals indicative of electro-cardiac activity of the patient. A single channel ECG implementation is shown here but multiple channel configurations are applicable also. The portable event recorder comprises a rugged case of molded plastic or the like having a suitable clip (not shown) for belt-attachment. Jacks 28, such as 3.5 mm connectors, are provided in this case for connecting the electrode leads to internal circuitry of the event recorder. The case includes a speaker 30 for transmission of the recorded signals to the telephone for upload to the central facility.

Figure 2A:
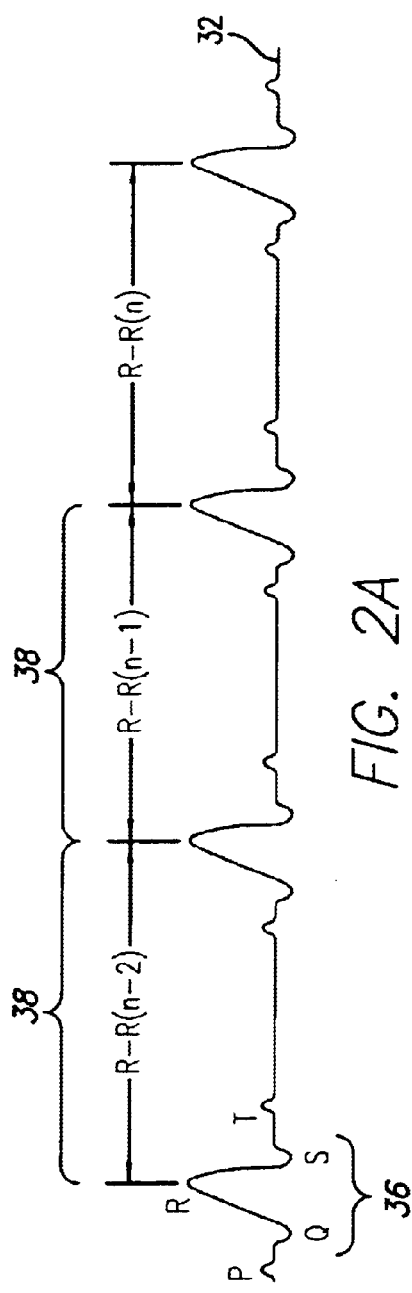
FIGS. 2A and 2B are views of two typical cardiac rhythms showing the QRS complexes for each, one showing a bigeminy and the other showing a healthy patient.
Figure 2B:
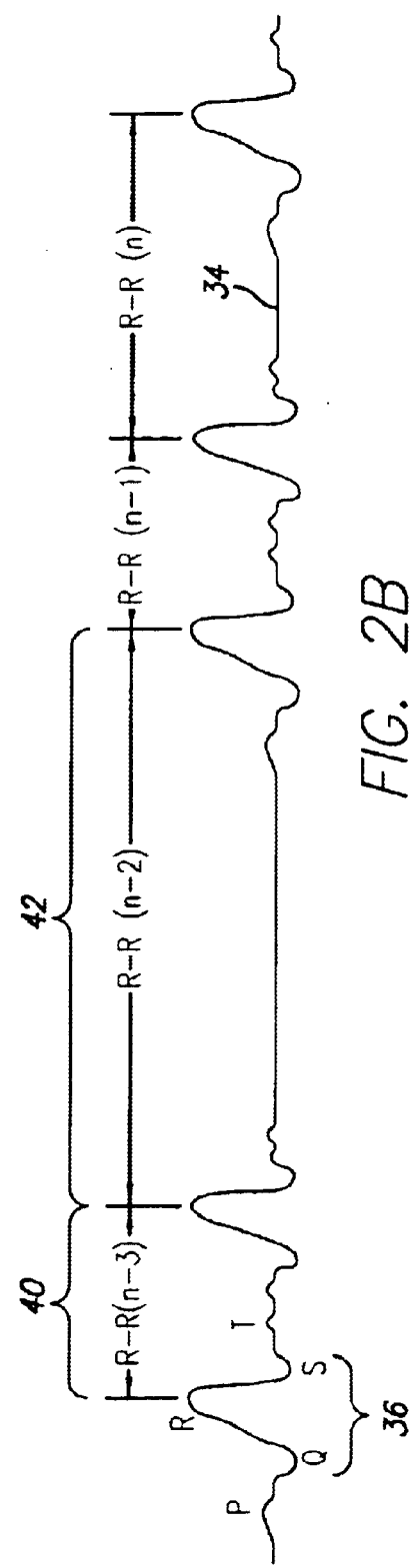

Referring now to FIGS. 2A and 2B, two graphs 32 and 34 of cardiac rhythms are shown. These may be thought of as expressing electro-cardiac activity data about the patient. Both contain views of a typical QRS complex 36. A "typical" QRS complex of the type illustrated in FIGS. 2A and 2B includes an atrial "P" component that has a small positive amplitude, as on the order of 50 to 100 microvolts, and a relatively short duration, as on the order of forty to eighty milliseconds. Thereafter, following a brief interval of quiescence on the order of 150 milliseconds, the signal cycles through a "QRS" complex corresponding to depolarization of the cardiac muscle in which the signal swings briefly negative in the "Q" component, then a relatively sharp positive spike of about one millivolt in the "R" component, and thereafter through a brief negative swing in the "S"

component. A nominal formal QRS duration of 100 milliseconds is typical. After another brief quiescent interval on the order or 200 milliseconds, a slight positive swing corresponding to the "T" component indicates repolarization of the cardiac muscle. The interval between cardiac rhythm signals is the inverse of the pulse rate and would be one second, for example, for a typical cardiac rhythm at sixty beats per minute.

In the cardiac rhythm of FIG. 2A, the beats are approximately equally spaced and the R—R intervals 38 will be approximately equal. In the cardiac rhythm of FIG. 2B, the beats are not equally spaced. Two beats are closer to each other than a following beat. The R—R intervals will therefore vary. The R—R interval 40 between two closer beats is shorter than the R—R interval 42 between two longer beats. In accordance with an aspect of the invention, the R—R interval is monitored to determine the existence of an AFIB event.

It will be appreciated by persons skilled in the analysis and treatment of cardiovascular disorders that the graph of FIG. 2A illustrates a somewhat idealized rhythm signal for a healthy individual. For patients exhibiting some form of cardiac disorder the rhythm signal may vary substantially from that shown in FIG. 2A. Indeed, for patients who have suffered permanent heart damage, one or more of the Q, R, and S components may be exaggerated or obliterated. Thus, for purposes of the present description and the appended claims, the term "QRS" with reference to rhythm signal components must be read in its broadest aspects as representing the signal that results from the patient's electrical ventricular depolarization. Similarly, the term "R—R interval" signifies the interval between successive rhythm signals, and need not necessarily be measured between identifiable "R" signal components, although that may be the case in certain measurements.

Figures 1, 3:
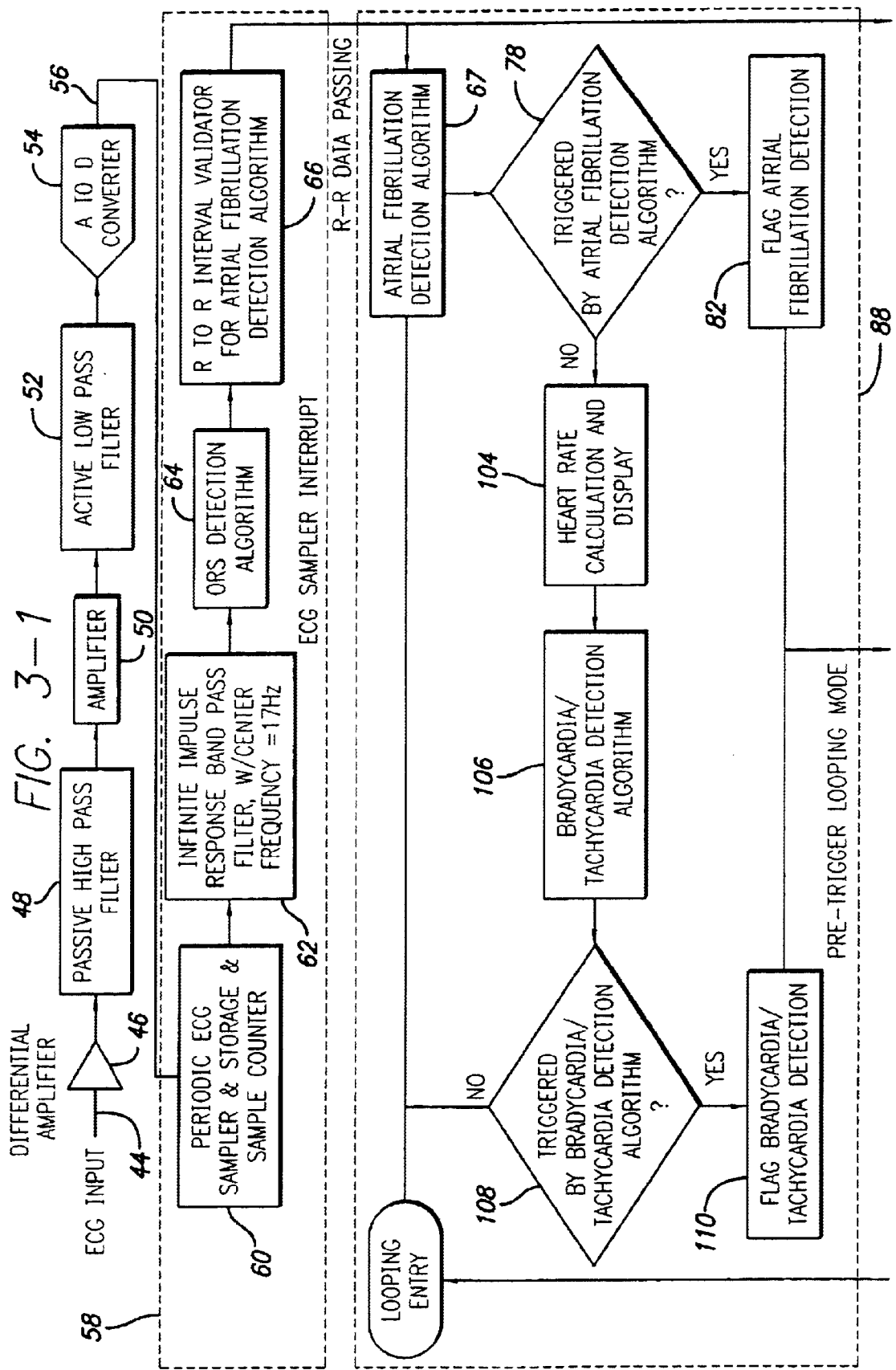
FIG. 3 is a functional block diagram of a cardiac event recorder incorporating aspects of the invention
Figures 2, 3:
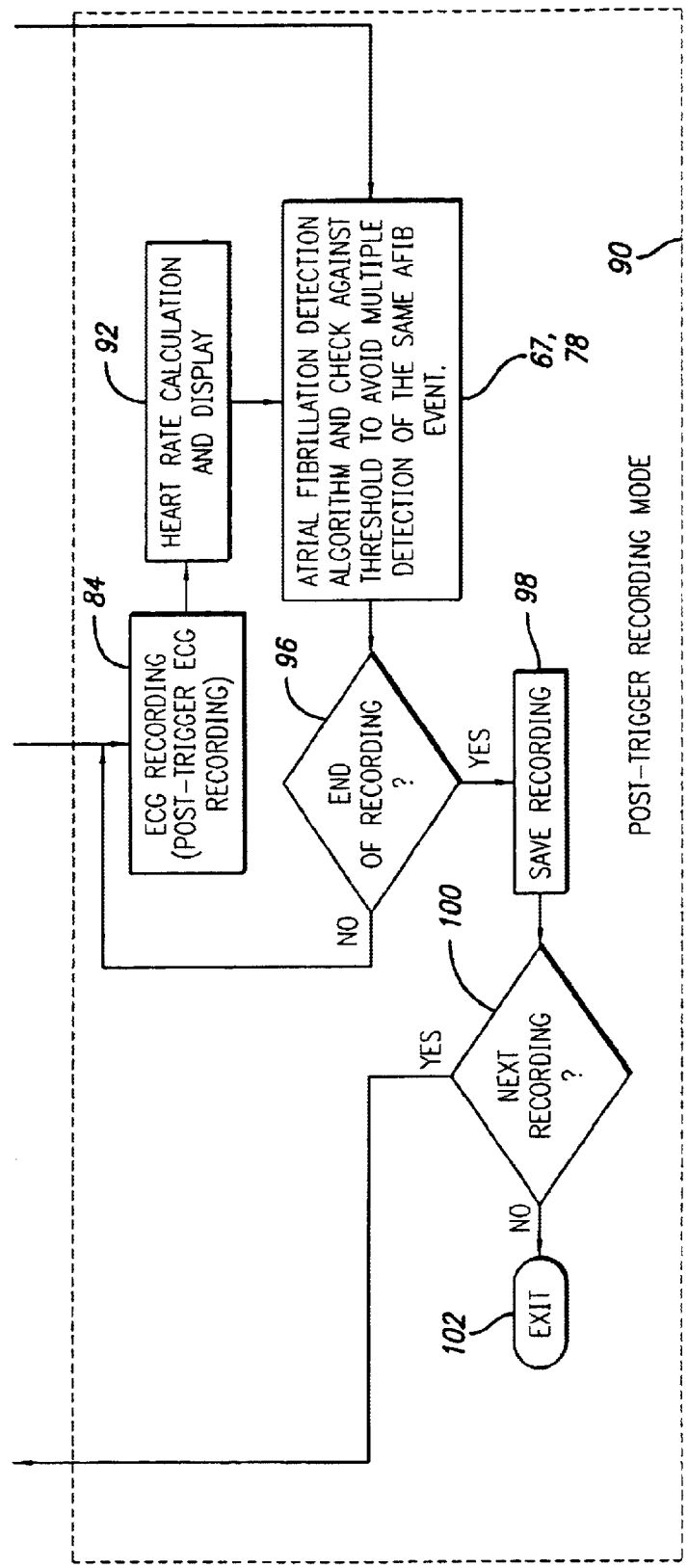

FIG. 3 illustrates an overview, block diagram of an event recorder 22 in accordance with aspects of the invention. Both a method of analyzing the cardiac rhythms of a patient to detect the presence of atrial fibrillation and a portable apparatus for analyzing cardiac rhythms of a patient to detect atrial fibrillation are discussed in relation to FIGS. 3 and 4. The electrodes 24 (FIG. 1) conduct ECG signals from the patient's skin through a lead set 26 as the ECG input 44 to a differential amplifier 46 for amplification. The amplified ECG signals are filtered in a high pass filter 48, amplified again 50, and filtered and amplified 52 again, this time in a low pass filter with amplifier. The amplified and filtered signals are then sampled in an analog-to-digital converter 54 and digital representative signals 56 provided. The digitized signals 56 are then processed in an ECG sampler interrupt 58. In this embodiment, the interrupt includes a periodic ECG sampler and storage and sample counter 60, well known in the art. The interrupt 58 also includes an infinite impulse response band pass filter 62 with a center frequency of 17 Hz in this embodiment. The filtered digital signals are then input to a QRS detector 64. The infinite impulse response band pass filter 62 and QRS detector 64 are also well known in the art and no further detail is provided here.

Outputs of the QRS detector 64 include R—R intervals, as discussed above in relation to FIGS. 2A and 2B, and other data, such as the heart rate, as required. This QRS signals are conducted to an R—R interval validator 66 for the atrial fibrillation detection system.

The analysis of the R—R intervals to detect an AFIB event is performed according to certain aspects of the invention, as is described below. In particular, certain ratios of R—R intervals are taken, and moving averages of those ratios are continually updated. Those averages are processed in accordance with aspects of the invention and from that processing, an AFIB event is determined.

Figure 4:
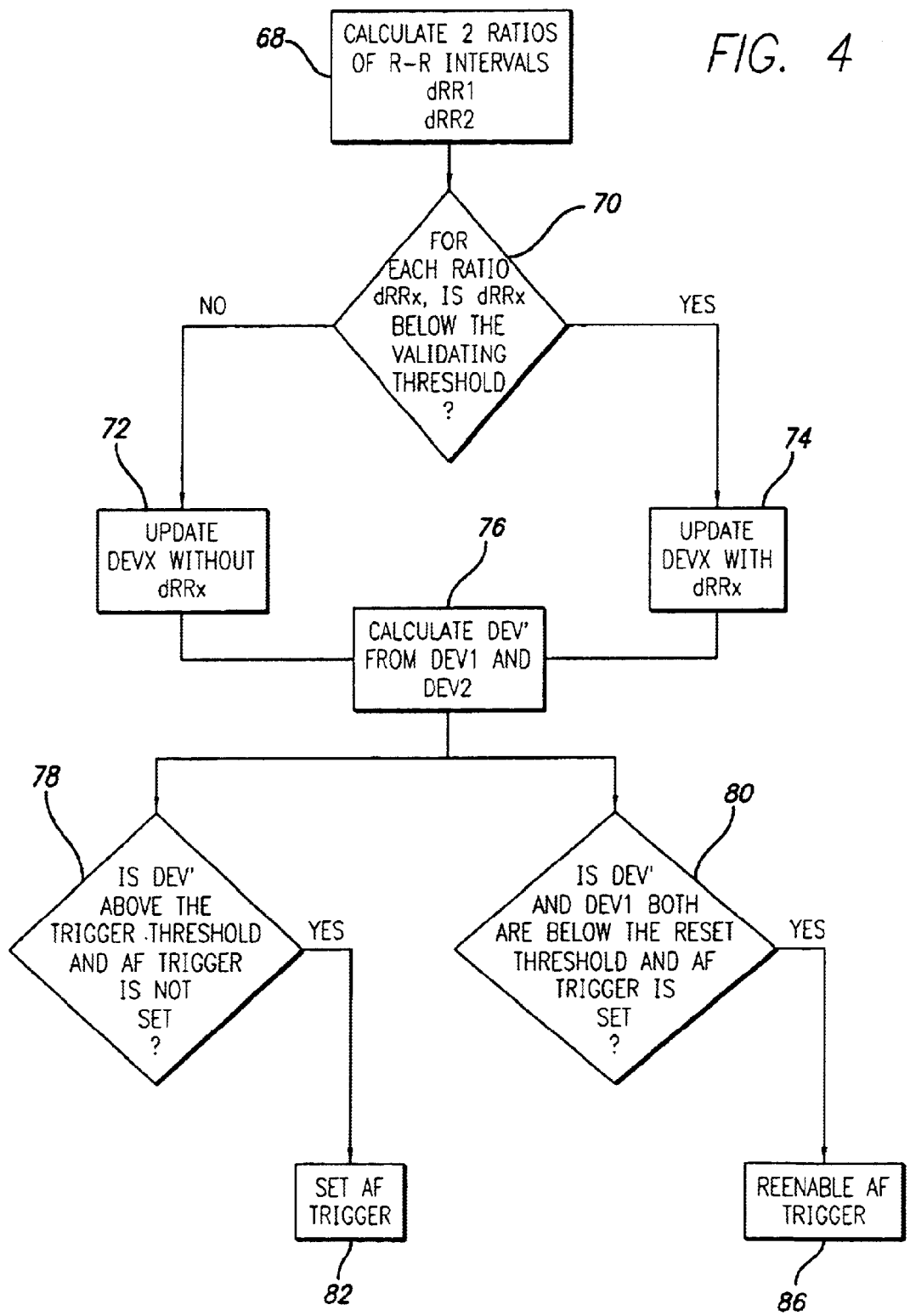
FIG. 4 is a functional block diagram of a validation of R—R interval ratios and an AFIB detector in accordance with aspects of the invention.

With continued reference to both FIGS. 3 and 4, the R—R interval validator 66 continually analyzes the R—R intervals presented by the QRS detector 64. In particular, two ratios of different R—R intervals are taken in an effort to eliminate any effects of premature ventricular contractions, couplets, and missed QRS detection, as shown in FIG. 4 in box 68. In this embodiment, two ratios are taken as follows:

$$dRR1(n) = \frac{RR(n)}{RR(n-1)} \qquad (1)$$

$$dRR2(n) = \frac{RR(n)}{RR(n-2)} \qquad (2)$$

where: RR(n)=the R—R interval between the current and preceding QRS complexes

RR(n−1)=the R—R interval between the preceding and second preceding QRS complexes RR(n−2)=the R—R interval between the second preceding and third preceding QRS complexes dRRx(n)=the current ratio of the respective R—R intervals In another aspect, the numerators of the above equations are exchanged with the denominators in the cases where the numerators are smaller than the denominators so that the result of the comparison is always 1 or greater. This is expressed as:

$$dRRx(n) = \max\left[\frac{RR(n)}{RR(n-x)}, \frac{RR(n-x)}{RR(n)}\right] \qquad (3)$$

where: x=the respective number associated with that particular ratio (for example, dRR1(n), RR(n−2))

The ratios are then compared to a validating threshold as shown in box 70. If either ratio dRRx is equal to or exceeds the validating threshold, a PVC or QRS detection error is indicated and the exponential moving average of the R—R interval for that ratio will be updated without reference to the present R—R interval as shown in box 72. For example, the validating threshold in one embodiment was set at 1.67. This value was derived from optimizing the performance based on actual clinical data. When either ratio equals or exceeds the validating threshold, the exponential moving average of that ratio is updated as follows:

$$Devx(n)=Devx(n-1)-\text{compensating factor} \qquad (4)$$

where: Devx(n)=the present exponential moving average of the R—R interval

Devx(n−1)=the exponential moving average of the R—R interval one interval ago

Compensating Factor=a constant found by optimization against a selected, standardized ECG data base. For example, in one embodiment, the compensating factor was 0.025 x=the respective number associated with that particular average (for example, Dev1(n), Dev2(n))

It can be noted that the exponential moving average Devx(n) will decrease and that the current R—R interval plays no part in determining the current value of the exponential moving average. That R—R interval, and that ratio, are effectively excluded from the average. There is no inclusion of the ratio in the respective average. This approach compensates for rhythms other than AFIB.

If a ratio is below the validating threshold, the exponential moving average for that ratio is updated, as shown in box 74, according to:

$$Devx(n)=[k*Devx(n-1)]+[(1-k)*(dRRx(n)-1)^2] \quad (5)$$

where: Devx(n)=the present exponential moving average k=a constant for controlling the length of averaging. In one embodiment, the constant was set at 0.987 for approximately 60 intervals of averaging Devx(n−1)=the previous exponential moving average taken at the preceding R—R interval dRRx(n)=the ratio value (always 1 or greater)

x=the respective number associated with that particular average and ratio (for example, Dev1(n), dRR1(n))

As mentioned, the length of averaging is determined from the selection of the value of "k." In one embodiment, the effect of "k" is shown in the following equation:

$$N = \frac{1}{(1-k)} \quad (6)$$

where: N=the number of R—R intervals k=the constant described above

Thus where k=0.987, N=76.9.

It can be noted that the exponential moving average for this ratio will be updated to include the present ratio value (dRRX(n)). As stated, the constant "k" controls the length of the averaging and was selected to be 0.987 in this embodiment, which corresponds to about a sixty interval average. The number of intervals averaged may be altered from sixty in other embodiments. In one embodiment, "k" may vary within the range of 0.900 to 0.995 for a range of 10 to 200 beats. However, it should be noted that if the number of intervals averaged is too few, the amount of false triggers may increase to an undesirable level. If the number of intervals averaged is too many, actual AFIB events may be missed.

The two exponential moving averages are then analyzed to determine if an AFIB event is present. This is done in the AFIB detection algorithm 67 also called the AFIB detector 67 or the AFIB processor 67. In this embodiment, as shown in box 76, the two exponential moving averages are combined into a Dev', which is calculated as follows:

$$Dev'=Dev1-\alpha\|Dev1-Dev2\| \quad (7)$$

where: Dev'=the difference average

Dev1=the exponential moving average of the first ratio

α=a compensating factor preventing false triggering on irregular rhythms other than AFIB. It is a positive constant found through clinical data optimization, and in one embodiment, was a value of 2

Dev2=the exponential moving average of the second ratio

The AFIB processor 67 then compares Dev' to a trigger threshold in this embodiment as shown in box 78. In this embodiment, the trigger threshold was set at 0.029 and if Dev'>0.029, an AFIB event has been detected, an AFIB trigger is set 82, and a record signal is sent to the memory 44 to capture and record a selected amount of electro-cardiac activity data, such as cardiac rhythms or QRS complexes, prior to and after the AFIB event as shown in box 84. A different value may be selected for the trigger threshold; however, if set too low, false triggers may increase to an undesirable level and if set too high, actual AFIB events may be missed. All the above, except actual ECG recording, is performed in the pre-trigger loop mode 88.

Once triggered by detecting an AFIB event, the AFIB processor 67 is unable to trigger again until Dev' and Dev1 both (in this embodiment) fall below a second threshold 80, which may be referred to as a "reset" threshold. Once Dev' and Dev1<0.017, the AFIB processor 67 is reset 86 and another AFIB event may be captured. It should be noted that in box 78, an AF trigger (box 82) cannot be set unless the Dev' is greater than the trigger threshold AND the AFIB trigger is not already set. If it is set, no new trigger, and no new recording for AFIB (box 84) can occur. Only if the trigger is reset in box 86 can a new trigger be set and recording begin again. Setting the reset threshold at a value other than the trigger threshold avoids the problem of recording the same AFIB event as multiple AFIB events as Dev' typically varies somewhat above and below 0.029.

It will be noted that the calculation of Dev' effectively compares the first exponential moving average (Dev1) to the second exponential moving average (Dev2) to determine how similar they are to each other. As shown above, the averages, in this case exponential moving averages, are averages of ratios of R—R intervals. All R—R intervals used in the ratios have fixed temporal relationships to each other. Thus the first ratio is a ratio of the current R—R (RR(n)) interval to the immediately preceding R—R interval (RR(n−1)), and the first average is an average of a plurality of these ratios. The second ratio is a ratio of the current R—R interval (RR(n)) to the second preceding R—R interval (RR(n−2)), and the second average is an average of a plurality of these ratios. Thus an analysis of Dev' equation (7) will show that regularly recurring cardiac arrhythmia will be effectively nullified or ignored.

In the case where the two averages are similar or equal, the last term of equation (7) will be zero or approximately zero and the Dev' term will be substantially equal to Dev1. However, where bigeminy and trigeminy are involved, the last term will rise in value. The recurring nature of bigeminy and trigeminy will result in a recurring difference between the R—R intervals that will be reflected in the ratios. The second average, which comprises second preceding R—R intervals in the ratio, will become larger. Because of that second, rising average (Dev2) and that fact that it is subtracted from the Dev1 term, and that the absolute value is taken, the value of Dev' will decrease below Dev1. Thus, bigeminy and trigeminy, as well as other regularly recurring arrhythmia will not raise the value of Dev' and result in a false AFIB detection. The AFIB processor 67 effectively ignores such arrhythmia. In effect, regularly recurring arrhythmia, such as bigeminy and trigeminy, are nullified by the use of the last term in equation (7).

Different approaches may be taken at averaging the ratios shown above. The exponential moving average was chosen in this embodiment because it presents a very efficient use of processing resources, a feature highly desirable in battery-powered, portable units. Likewise, other elements may be changed according to the results desired. The constant "k" may be changed to consider more, or fewer, cardiac rhythms in calculating the exponential moving averages, as was discussed. The "penalty" equation (4) used to update the respective exponential moving average without regard to the current R—R interval may have the value of its compensating factor (0.025 in one embodiment) changed to another value depending on the optimization required. Likewise, the various thresholds selected above may be altered as desired for different performance. The threshold selected above were optimized for a particular data base performance. The use of an exponential moving average for comparison of R—R intervals has the advantage of tracking relatively slow changes in cardiac rhythm associated with changes in patient activities while lowering the amount of false alarm indications.

After an AFIB event has been flagged or triggered 82, the method moves into the post-trigger recording mode 90. ECG recording is performed 84 to capture an AFIB event. Additionally, the heart rate is calculated and displayed 92 on a display 94 (FIG. 1). The heart rate may be calculated from the R—R intervals, as is well known. The AFIB detection occurs 78, as previously described and the end of recording is checked 96. In one embodiment, forty-five seconds of QRS complexes occurring prior to the detected AFIB event are recorded as are fifteen seconds of QRS complexes after the detected AFIB event. These data are recorded in a looping memory, as is well known in the art. In such a memory, data may be continuously recorded until an "event" is flagged, which is then recorded with a non-overwrite flag. Once such an event has been recorded, the memory contents may be uploaded to the medical monitoring service center of the patient for interpretation and additional diagnostics. In one embodiment, the data representative of an AFIB event is specially marked in the memory of the portable event recorder so that when it is uploaded, the monitoring service can quickly locate all recorded AFIB events in the uploaded data. In one case, a special data marker of five pulses is recorded at the location of the AFIB event data.

An indication may also be provided to the patient that AFIB event data has been recorded. In one embodiment, an audible alert is given in the form of a beeping tone that repeats once each minute. The tone may also be used to alert the patient that bradycardia or tachycardia data has been recorded. The purpose is to alert the patient that an upload of data to the central monitoring service may be made. To terminate the tone alert, the patient either uploads the data or cycles the power switch of the portable event recorder 22. A visual alert that event data is present in memory may also be made in the display 94 of the event recorder 22 (FIG. 1). On the other hand, the patient may desire to record further AFIB events, or other data, before an upload occurs and the patient may continue to use the event recorder 22 until a certain time period has passed or until the memory is full or at least fuller. Different memories may be used and different amounts of data surrounding an AFIB event may be recorded in other embodiments.

If the required amount of recording has occurred 96, the data is flagged 98 for saving and the method proceeds to the next recording 100, or if the memory is full, the patient is notified through a visual display 28 and/or through an audible means, such as by a tone transmitted through the speaker 30 (FIG. 1) and the method moves to exit 102.

Returning to FIG. 3, if the AFIB detector 67 does not detect an AFIB event 78, the heart rate is calculated and displayed 104 on the display 94 (FIG. 1). The QRS complex signals are also conducted to a bradycardia/tachycardia detector 106 in this embodiment. If either a bradycardia or a tachycardia is detected 108, data is flagged 110 for recording 84, as described before. If no bradycardia or tachycardia is detected 106 and no trigger results 108, the method and apparatus loops back to the AFIB detector 67.

As a brief review of the foregoing then, in FIG. 3 there is illustrated an embodiment of an event recorder 22 comprising a differential input amplifier 46, connected to conventional cardiac electrodes 24 (FIG. 1) suitably positioned on a patient 20. The output of the differential input amplifier, through a passive high pass filter 48, an amplifier 50, and an active low pass filter 52, is connected to the input of an analog-to-digital converter 54. The output of the analog-to-digital converter is connected to a micro-controller. A timer of the micro-controller is configured as a periodic interrupt, which periodically samples ECG signals 60, stores the ECG signals 60, keeps the counter of the samples 60, band pass filters ECG signals 62 for a reliable QRS detection 64, validates the R—R intervals 66, and passes the R—R interval values to the looping mode 88, or to the recording mode 90 for the atrial fibrillation detector 67.

The looping mode 88 periodically runs the atrial fibrillation detector 67, heart rate calculation and display function 104, and the bradycardia/tachycardia detection function 106. If an atrial fibrillation or a bradycardia/tachycardia event is detected, the atrial fibrillation detection indicators 82 or the bradycardia/tachycardia detection indicators 110 are set accordingly, and the recording mode 90 is executed. The recording mode 90 periodically runs the atrial fibrillation detection algorithm 67 and 78 to check against the threshold and to set indications to avoid multiple detection of the same atrial fibrillation event.

In one embodiment, an 8-bit microprocessor or microcontroller was used. The microprocessor was made by NEC and had a model number of D78P064GC or D78P0308GC. However, other 8-bit microprocessors may be used including those made by Mitsubishi and Hitachi.

In view of the above therefore, a method and an apparatus in accordance with the invention provide automatic triggering on an AFIB event as well as fast triggering. While the speed of triggering on an AFIB event can be controlled by the selection of certain parameters, as was discussed above, the inventors have found that fast triggering was achieved in accordance with the embodiment disclosed above. Because of the use of exponential moving averages, a looping memory, and other power saving techniques, the method and apparatus of the invention are perfectly suited to a portable application.

Figure 5:
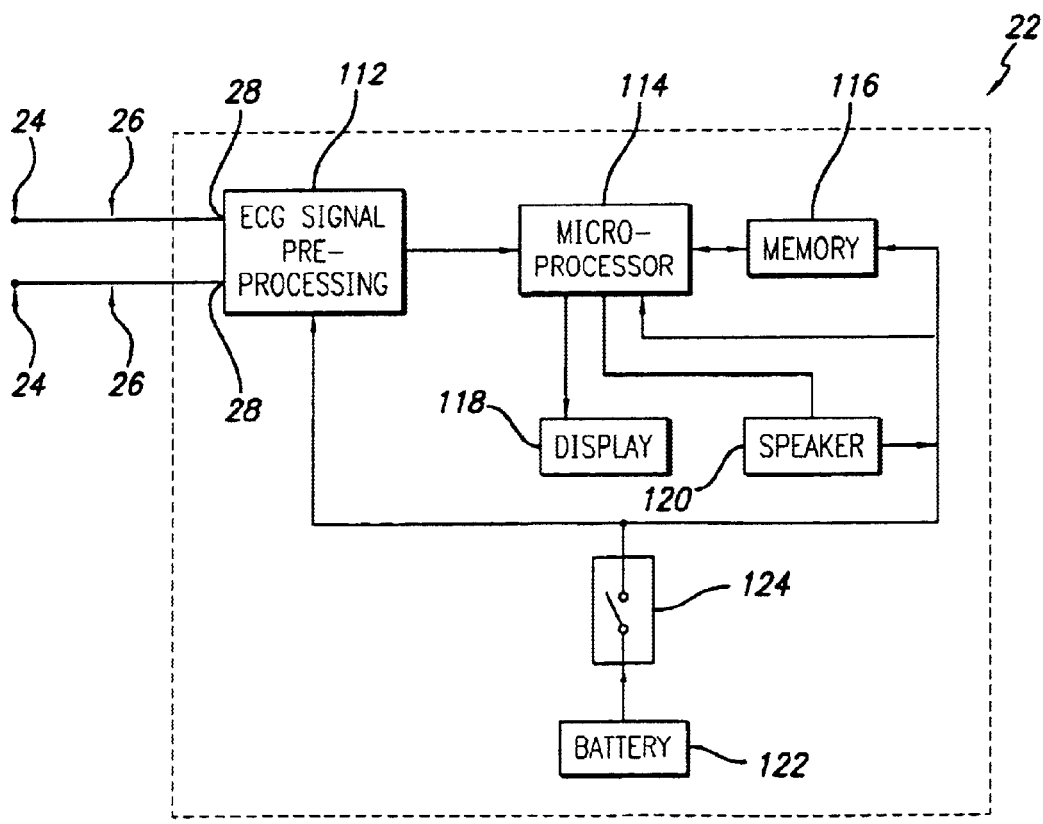
FIG. 5 is a general block diagram of a portable apparatus for analyzing cardiac rhythms of a patient to detect atrial fibrillation in accordance with aspects of the invention showing the various hardware functions and their interconnections.

Turning now to FIG. 5, a portable apparatus for analyzing cardiac rhythms of a patient to detect atrial fibrillation is shown. In particular, an event recorder 22 is shown connected to two electrodes 24 through a lead set 26 to obtain electro-cardiac activity data from the patient. The lead set 26 is connected to the event recorder 22 through jacks 28. The portable event recorder comprises the ECG signal preprocessing section 112 that provides QRS complex data and other data to a microprocessor or micro-controller 114. The microprocessor 114 analyzes the QRS data, in particular the R—R intervals, as described above, to detect the existence of an AFIB event in the patient.

The microprocessor interfaces with a memory 116 that is used to capture and record arrhythmia events detected by the event recorder 22. The microprocessor also controls the output of a display device, such as a low power, liquid crystal display 118, and the audio output of a speaker 120. For example, the patient alerts that AFIB data has been recorded in memory 116 and that an upload of data can be made to the central monitoring station can be communicated through the speaker. The patient's heart rate may be communicated by the processor through the display 118. Power is provided by a portable battery 122 through an on/off switch 124.

It will be appreciated that the present invention offers particular advantages when utilized in a portable battery operated unit since it is maintained in a non-recording state until an arrhythmia is detected, at which time recording begins but continues only for a limited duration bracketing the detected AFIB event. The loop memory then returns to non-recording conditions until the next detected arrhythmia. This minimizes battery drain and, very importantly, allows monitoring over long intervals, greater than twenty-four hours, since the amount of memory used depends only upon the number and frequency of detected arrhythmias. These highly desirable attributes are optimized by the present invention because, as previously described, the present invention is based in large part on the recognition that clinically significant arrhythmias can be detected using the R—R interval.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A method of analyzing the cardiac rhythms of a patient to detect the presence of atrial fibrillation, the method comprising:
   measuring R—R intervals between a plurality of QRS complexes of the patient, including present and preceding QRS complexes;
   comparing the present R—R interval to the preceding R—R interval to result in a first ratio;
   comparing the present R—R interval to the second preceding R—R interval to result in a second ratio;
   comparing the first ratio and the second ratio to a validating threshold;
   calculating a first average of R—R intervals of the plurality of QRS complexes without including the present R—R interval in the first average if the first ratio exceeds the validating threshold;
   calculating the first average of R—R intervals with inclusion of the present R—R interval in the first average if the first ratio is less than or equal to the validating threshold;
   calculating a second average of R—R intervals of the plurality of QRS complexes without inclusion of the present R—R interval in the second average if the second ratio exceeds the validating threshold;
   calculating the second average of R—R intervals with inclusion of the present R—R interval in the second average if the second ratio is less than or equal to the validating threshold; and
   determining the presence of an atrial fibrillation by analyzing the first and second averages.

2. The method of analyzing cardiac rhythms of claim 1 wherein the steps of calculating the first average comprise calculating exponential moving averages for the first average.

3. The method of analyzing cardiac rhythms of claim 1 wherein the steps of calculating the second average comprises calculating exponential moving averages for the second average.

4. The method of analyzing cardiac rhythms of claim 1 wherein the step of comparing the first ratio and the second ratio to a validating threshold comprises selecting the validating threshold so that R—R intervals caused by premature ventricular contractions and other irregular rhythms, other than AFIB, are excluded from the first and second averages.

5. The method of analyzing cardiac rhythms of claim 4 wherein the first and second ratios are formed in accordance with the following:

$$dRR1(n) = \frac{RR(n)}{RR(n-1)}$$

$$dRR2(n) = \frac{RR(n)}{RR(n-2)}$$

where: RR(n)=the R—R interval between the current and preceding QRS complexes
   RR(n−1)=the R—R interval between the preceding and second preceding QRS complexes
   RR(n−2)=the R—R interval between the second preceding and third preceding QRS complexes
   dRRx(n)=the current ratio of the respective R—R intervals.

6. The method of analyzing cardiac rhythms of claim 1 further comprising the step of determining a difference average in accordance with:

$$Dev'=Dev1-\alpha\|Dev1-Dev2\|$$

where: Dev'=the difference average
   Dev1=the first average
   α=a compensating factor preventing false triggering on irregular rhythms other than AFIB
   Dev2=the second average.

7. The method of analyzing cardiac rhythms of claim 1 further comprising:
   combining the first average and the second average to result in a difference average; and
   the step of determining the presence of an atrial fibrillation comprises comparing the difference average to a trigger threshold and if the difference average exceeds the trigger threshold, providing an indication that atrial fibrillation exists.

8. The method of analyzing cardiac rhythms of claim 7 wherein the step of combining the first and second averages further comprises substantially nullifying regularly recurring irregular cardiac rhythms in determining the difference average.

9. The method of analyzing cardiac rhythms of claim 8 wherein the step of nullifying regularly recurring irregular cardiac rhythms comprises nullifying bigeminy and trigeminy cardiac rhythms in determining the difference average.

10. The method of analyzing cardiac rhythms of claim 7 further comprising the step of preventing the detection of an additional atrial fibrillation until the difference average is less than a reset threshold, the reset threshold being different from the trigger threshold.

11. The method of analyzing cardiac rhythms of claim 10 further comprising the step of preventing the detection of an additional atrial fibrillation until the first average is also less than the reset threshold.

12. The method of analyzing cardiac rhythms of claim 10 further comprising selecting the reset threshold to be a value that is far enough below the trigger threshold such that the step of providing an indication that atrial fibrillation exists is given substantially only for different occurrences of atrial fibrillation events in the patient.

13. The method of analyzing cardiac rhythms of claim 7 further comprising:
   recording QRS complex data in the event that an indication is provided that atrial fibrillation exists; and
   preventing the recording of data until the difference average is less than a reset threshold, the reset threshold being different from the trigger threshold.

14. The method of analyzing cardiac rhythms of claim 1 wherein the steps of calculating the averages without inclusion of the present R—R interval comprises reducing the average from the previous average.

15. The method of analyzing cardiac rhythms of claim 1 wherein the steps of comparing the current R—R interval to the preceding R—R intervals comprise selecting the numerators and denominators of the ratios so that the results of the ratios are always equal to or greater than one.

16. The method of analyzing cardiac rhythms of claim 15 wherein the step of selecting the numerators and denominators of the comparisons is performed in accordance with:

$$dRRx(n) = \max\left[\frac{RR(n)}{RR(n-x)}, \frac{RR(n-x)}{RR(n)}\right]$$

where: dRRx(n)=the particular ratio being taken at time "n"
n=time
RR(n)=R—R interval current in time
RR(n-x)=an R—R interval preceding in time, where x=1 or 2
x=the respective number associated with that particular ratio and R—R interval (for example, dRR1(n), RR(n-1)).

17. The method of analyzing cardiac rhythms of claim 1 wherein the steps of calculating averages each further comprises the step of adjusting the length of averaging by selecting the number of R—R intervals in the averages so that false atrial fibrillation detections are reduced and missed detections of atrial fibrillations are reduced.

18. The method of analyzing cardiac rhythms of claim 17 wherein the step of selecting the number of R—R intervals used in calculating averages is selected to be approximately sixty.

19. A method of detecting atrial fibrillation in a patient, the method comprising:
  measuring R—R intervals between a plurality of QRS complexes of the patient, including present and preceding QRS complexes;
  forming a first ratio by dividing an R—R interval into another R—R interval in which one R—R interval is the present interval and one R—R interval is a preceding interval;
  forming a second ratio by dividing an R—R interval into another R—R interval in which one R—R interval is the present interval and one R—R interval is a preceding interval different from the preceding interval used in the first ratio;
  averaging a plurality of first ratios to form a first average;
  averaging a plurality of second ratios to form a second average;
  analyzing the difference between the first and second averages;
  comparing the difference between the averages to a threshold to determine if an atrial fibrillation exists in the patient.

20. The method of detecting atrial fibrillation of claim 19 wherein:
  the step of analyzing the difference comprises combining the first average and the second average to result in a difference average; and
  the step of comparing the difference comprises comparing the difference average to a trigger threshold and if the difference average exceeds the trigger threshold, providing an indication that atrial fibrillation exists.

21. The method of detecting atrial fibrillation of claim 20 wherein the step of combining the first and second averages further comprises substantially nullifying regularly recurring irregular cardiac rhythms in determining the difference average.

22. The method of detecting atrial fibrillation of claim 21 wherein the step of nullifying comprises subtracting a factor representative of regularly recurring irregular cardiac rhythms.

23. The method of detecting atrial fibrillation of claim 21 wherein the step of nullifying regularly recurring irregular cardiac rhythms comprises nullifying bigeminy and trigeminy cardiac rhythms in determining the difference average.

24. The method of detecting atrial fibrillation of claim 20 further comprising the step of preventing the detection of an additional atrial fibrillation until the difference average is less than a reset threshold, the reset threshold being different from the trigger threshold.

25. The method of detecting atrial fibrillation of claim 24 further comprising the step of preventing the detection of an additional atrial fibrillation until the first average is also less than the reset threshold.

26. The method of detecting atrial fibrillation of claim 24 further comprising selecting the reset threshold to be a value that is far enough below the trigger threshold such that the step of providing an indication that atrial fibrillation exists is given substantially only for different occurrences of atrial fibrillation events in the patient.

27. The method of detecting atrial fibrillation of claim 24 further comprising:
  recording QRS complex data in the event that an indication is provided that atrial fibrillation exists; and
  preventing the recording of data until the difference average is less than a reset threshold, the reset threshold being different from the trigger threshold.

28. The method of detecting atrial fibrillation of claim 19 wherein the steps of calculating averages each further comprises the step of adjusting the length of averaging by selecting the number of R—R intervals in the averages so that false atrial fibrillation detections are reduced and missed detections of atrial fibrillations are reduced.

29. The method of detecting atrial fibrillation of claim 19 further comprising the steps of:
  comparing the first ratio and the second ratio to a validating threshold;
  calculating the first average without including the present R—R interval in the first average if the first ratio exceeds the validating threshold;
  calculating the first average with inclusion of the present R—R interval in the first average if the first ratio is less than or equal to the validating threshold;
  calculating the second average without inclusion of the present R—R interval in the second average if the second ratio exceeds the validating threshold; and
  calculating the second average with inclusion of the present R—R interval in the second average if the second ratio is less than or equal to the validating threshold.

30. A portable apparatus for detecting atrial fibrillation in a patient, the apparatus comprising:
  a plurality of electrodes adapted for placement on the patient for developing electrical signals indicative of cardiac rhythms; and
  a portable unit comprising a housing within which is located:

a battery for providing power to the portable unit;

means for measuring R—R intervals of a plurality of QRS complexes of the electrical signals from the patient, including present and preceding QRS complexes;

means for forming a first ratio by dividing an R—R interval into another R—R interval in which one R—R interval is the present interval and one R—R interval is a preceding interval;

means for forming a second ratio by dividing an R—R interval into another R—R interval in which one R—R interval is the present interval and one R—R interval is a preceding interval different from the preceding interval used in the first ratio;

means for averaging a plurality of first ratios to form a first average;

means for averaging a plurality of second ratios to form a second average;

means for analyzing the difference between the first and second averages;

means for comparing the difference between the averages to a threshold to determine if an atrial fibrillation exists in the patient.

31. The portable apparatus for detecting atrial fibrillation of claim 30 wherein:

the means for analyzing the difference is also for combining the first average and the second average to result in a difference average; and the means for comparing the difference is also for comparing the difference average to a trigger threshold and if the difference average exceeds the trigger threshold, for providing an indication that atrial fibrillation exists.

32. The portable apparatus for detecting atrial fibrillation of claim 31 wherein the means for combining the first and second averages is further for substantially nullifying regularly recurring irregular cardiac rhythms in determining the difference average.

33. The portable apparatus for detecting atrial fibrillation of claim 32 wherein the means for nullifying is also for subtracting a factor representative of regularly recurring irregular cardiac rhythms.

34. The portable apparatus for detecting atrial fibrillation of claim 32 wherein the means for nullifying regularly recurring irregular cardiac rhythms is also for nullifying bigeminy and trigeminy cardiac rhythms in determining the difference average.

35. The portable apparatus for detecting atrial fibrillation of claim 31 further comprising:

means for recording QRS complex data in the event that an indication is provided that atrial fibrillation exists; and means for preventing the recording of data until the difference average is less than a reset threshold, the reset threshold being different from the trigger threshold.

36. The portable apparatus for detecting atrial fibrillation of claim 35 further comprising means for preventing the recording of additional atrial fibrillation until the difference average is less than a reset threshold, the reset threshold being different from the trigger threshold.

37. The portable apparatus for detecting atrial fibrillation of claim 36 further comprising means for preventing the detection of an additional atrial fibrillation until the first average is also less than the reset threshold.

38. The portable apparatus for detecting atrial fibrillation of claim 36 further comprising means for selecting the reset threshold to be a value that is far enough below the trigger threshold such that an indication that atrial fibrillation exists is given substantially only for different occurrences of atrial fibrillation events in the patient.

39. The portable apparatus for detecting atrial fibrillation of claim 30 wherein the means for averaging further comprises means for adjusting the length of averaging by selecting the number of R—R intervals in the averages so that false atrial fibrillation detections are reduced and missed detections of atrial fibrillations are reduced.

40. The portable apparatus for detecting atrial fibrillation of claim 30 further comprising:

means for comparing the first ratio and the second ratio to a validating threshold;

means for calculating the first average without including the present R—R interval in the first average if the first ratio exceeds the validating threshold;

means for calculating the first average with inclusion of the present R—R interval in the first average if the first ratio is less than or equal to the validating threshold;

means for calculating the second average without inclusion of the present R—R interval in the second average if the second ratio exceeds the validating threshold; and means for calculating the second average with inclusion of the present R—R interval in the second average if the second ratio is less than or equal to the validating threshold.

41. A method for the detection of atrial fibrillation in a patient through analysis of electro-cardiac activity data, the method comprising:

measuring a plurality of R—R intervals between a plurality of QRS complexes of the patient, including present and preceding QRS complexes to thereby obtain a present R—R interval and preceding R—R intervals;

comparing the present R—R interval with a plurality of different preceding R—R intervals;

combining a plurality of such comparisons and providing a value representative of the combination;

comparing the value of the combination against a trigger threshold;

recording electro-cardiac activity data if the value exceeds the trigger threshold.

42. The method for the detection of atrial fibrillation of claim 41 wherein once the trigger threshold has been exceeded and recording has occurred, further comprising the step of preventing the further recording until the value of the combination has fallen below a reset threshold, the reset threshold being different than the trigger threshold.

43. The method for the detection of atrial fibrillation of claim 41 wherein the step of comparing R—R intervals comprises producing a quotient from each comparison, and further comprises comparing the quotient against a validating threshold;

if the quotient exceeds the validating threshold, then excluding the comparison from the step of combining.

44. The method for the detection of atrial fibrillation of claim 41 comprising:

comparing the present R—R interval with a first preceding R—R interval to result in a first comparison;

comparing the present R—R interval with a second preceding R—R interval to result in a second comparison, the second preceding R—R interval being different from the first R—R interval;

combining a plurality of first comparisons to result in a first combination having a first combination value;

combining a plurality of second comparisons to result in a second combination having a second combination value;

comparing the first combination value with the second combination value and providing a combination comparison value;

comparing the combination comparison value against the trigger threshold;

recording electro-cardiac activity data if the combination comparison value exceeds the trigger threshold.

45. The method for the detection of atrial fibrillation of claim 44 further comprising preventing the recording of data until the combination comparison value is less than a reset threshold, the reset threshold being different from the trigger threshold.

* * * * *